United States Patent
Myrick et al.

(10) Patent No.: US 9,182,282 B2
(45) Date of Patent: *Nov. 10, 2015

(54) MULTI-ANALYTE OPTICAL COMPUTING SYSTEM

(75) Inventors: Michael L. Myrick, Irmo, SC (US);
Robert P. Freese, Pittsboro, NC (US);
David L. Perkins, Irmo, SC (US);
Terrell Teague, Macedon, NY (US);
William Soltmann, Columbia, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 1044 days.

This patent is subject to a terminal disclaimer.

(21) Appl. No.: 12/447,591

(22) PCT Filed: Nov. 1, 2007

(86) PCT No.: PCT/US2007/083291
§ 371 (c)(1),
(2), (4) Date: Feb. 2, 2010

(87) PCT Pub. No.: WO2008/057912
PCT Pub. Date: May 15, 2008

(65) Prior Publication Data
US 2010/0141952 A1    Jun. 10, 2010

Related U.S. Application Data

(60) Provisional application No. 60/856,191, filed on Nov. 2, 2006.

(51) Int. Cl.
*G01N 21/00* (2006.01)
*G01J 3/28* (2006.01)
(Continued)

(52) U.S. Cl.
CPC .... *G01J 3/28* (2013.01); *G01J 3/02* (2013.01); *G01J 3/021* (2013.01); *G01J 3/0229* (2013.01);
(Continued)

(58) Field of Classification Search
USPC .................. 356/300, 303, 445, 448, 433–439
See application file for complete search history.

(56) References Cited

U.S. PATENT DOCUMENTS 3,632,435 A    1/1972    Eriksson et al.
3,717,078 A    2/1973    Ogura
(Continued)

FOREIGN PATENT DOCUMENTS

EP    0 600 334 A2    6/1996
EP    1969326 A1     9/2008
(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.
(Continued)

*Primary Examiner* — Gregory J Toatley
*Assistant Examiner* — Rebecca C Bryant
(74) *Attorney, Agent, or Firm* — Haynes and Boone, LLP (57) ABSTRACT

The present subject matter relates to methods of high-speed analysis of product samples. Light is directed to a portion of a product under analysis and reflected from or transmitted through the product toward an optical detector. Signals for the detector are compared with reference signals based on a portion of the illuminating light passing through a reference element to determine characteristics of the product under analysis. The products under analysis may be stationary, moved by an inspection point by conveyor or other means, or may be contained within a container, the container including a window portion through which the product illuminating light may pass.

19 Claims, 4 Drawing Sheets

(51) Int. Cl.
*G01J 3/02* (2006.01)
*G01J 3/08* (2006.01)
*G01J 3/42* (2006.01)
*G01J 3/12* (2006.01)

(52) U.S. Cl.
CPC ............ *G01J 3/0232* (2013.01); *G01J 3/0235* (2013.01); *G01J 3/0243* (2013.01); *G01J 3/08* (2013.01); *G01J 3/42* (2013.01); *G01J 2003/1213* (2013.01); *G01N 2201/128* (2013.01); *G01N 2201/1293* (2013.01)

(56) References Cited

U.S. PATENT DOCUMENTS

| | | |
|---|---|---|
| 3,761,724 A | 9/1973 | Dennis |
| 4,084,880 A | 4/1978 | Clow |
| 4,118,106 A | 10/1978 | Leith |
| 4,499,378 A | 2/1985 | Miyatake et al. |
| 4,595,832 A | 6/1986 | LaDelfe et al. |
| 4,607,914 A | 8/1986 | Fienup |
| 4,687,335 A | 8/1987 | Zupanick et al. |
| 4,687,337 A | 8/1987 | Stewart et al. |
| 4,704,536 A | 11/1987 | Sugiyama et al. |
| 4,821,338 A | 4/1989 | Naruse et al. |
| 4,891,574 A | 1/1990 | Nagaya et al. |
| 4,917,958 A | 4/1990 | Akai et al. |
| 4,934,782 A | 6/1990 | Soffer et al. |
| 4,968,148 A | 11/1990 | Chow et al. |
| 4,981,332 A | 1/1991 | Smith |
| 5,005,946 A | 4/1991 | Brandstetter |
| 5,029,245 A | 7/1991 | Keranen et al. |
| 5,071,526 A | 12/1991 | Pletcher et al. |
| 5,090,807 A | 2/1992 | Tai |
| 5,103,340 A | 4/1992 | Dono et al. |
| 5,137,364 A | 8/1992 | McCarthy |
| 5,150,236 A | 9/1992 | Patel |
| 5,194,921 A | 3/1993 | Tambo et al. |
| 5,223,715 A | 6/1993 | Taylor |
| 5,241,178 A * | 8/1993 | Shields .................... 250/339.02 |
| 5,259,381 A | 11/1993 | Cheung et al. |
| 5,289,289 A | 2/1994 | Nagaski |
| 5,321,539 A | 6/1994 | Hirbayashi et al. |
| 5,406,082 A | 4/1995 | Pearson et al. |
| 5,412,465 A | 5/1995 | Baylor et al. |
| 5,424,545 A | 6/1995 | Block et al. |
| 5,459,677 A | 10/1995 | Kowalski et al. |
| 5,479,164 A | 12/1995 | Yorks et al. |
| 5,504,332 A | 4/1996 | Richmond et al. |
| 5,513,022 A | 4/1996 | Son et al. |
| 5,555,128 A | 9/1996 | Khoury et al. |
| 5,622,868 A | 4/1997 | Clarke et al. |
| 5,641,962 A | 6/1997 | Perry et al. |
| 5,710,655 A | 1/1998 | Rumbaugh et al. |
| 5,717,605 A | 2/1998 | Komiya et al. |
| 5,734,098 A | 3/1998 | Kraus et al. |
| 5,737,076 A | 4/1998 | Glaus et al. |
| 5,747,806 A | 5/1998 | Khalil et al. |
| 5,750,994 A | 5/1998 | Schlager |
| 5,760,399 A | 6/1998 | Trygstad |
| 5,771,096 A | 6/1998 | Andersen |
| 5,781,289 A | 7/1998 | Sabsabi et al. |
| 5,799,231 A | 8/1998 | Gates et al. |
| 5,828,492 A | 10/1998 | Moser et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 | 3/2001 | Myrick et al. |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,573,999 B1 | 6/2003 | Yang |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Goetz et al. |
| 6,771,369 B2 | 8/2004 | Rzasa et al. |
| 6,776,517 B2 | 8/2004 | Afnan et al. |
| 6,798,518 B2 | 9/2004 | Difoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,348,493 B2 | 3/2008 | Osanai et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 7,993,276 B2 | 8/2011 | Nazarian et al. |
| 2001/0034064 A1 | 10/2001 | Turner et al. |
| 2002/0008215 A1 | 1/2002 | Evans |
| 2002/0050567 A1 | 5/2002 | Boudet et al. |
| 2002/0071118 A1 | 6/2002 | Shinbori et al. |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0197850 A1 | 10/2004 | Baer et al. |
| 2004/0227086 A1 | 11/2004 | Haug et al. |
| 2005/0077476 A1 | 4/2005 | Poteet et al. |
| 2005/0087132 A1 | 4/2005 | Dickey et al. |

(56) References Cited

U.S. PATENT DOCUMENTS

| | | | |
|---|---|---|---|
| 2005/0167264 A1 | 8/2005 | Sternbergh et al. | |
| 2005/0251289 A1 | 11/2005 | Bonney et al. | |
| 2005/0264815 A1 | 12/2005 | Wechsler et al. | |
| 2005/0288906 A1 | 12/2005 | Drennen, III et al. | |
| 2006/0035018 A1 | 2/2006 | Sakurai et al. | |
| 2006/0051036 A1 | 3/2006 | Treado et al. | |
| 2006/0093523 A1 | 5/2006 | Norman | |
| 2006/0142955 A1* | 6/2006 | Jones et al. | 702/32 |
| 2006/0153492 A1 | 7/2006 | Treves et al. | |
| 2006/0158734 A1 | 7/2006 | Schuurmans et al. | |
| 2006/0169902 A1 | 8/2006 | Watanabe | |
| 2006/0197015 A1 | 9/2006 | Sterling et al. | |
| 2006/0276697 A1 | 12/2006 | Demuth et al. | |
| 2007/0035737 A1 | 2/2007 | Andrews et al. | |
| 2007/0137292 A1 | 6/2007 | Xian et al. | |
| 2007/0201136 A1 | 8/2007 | Myrick | |
| 2007/0282647 A1 | 12/2007 | Freese et al. | |
| 2007/0294094 A1* | 12/2007 | Alessandrini et al. | 705/1 |
| 2008/0111064 A1 | 5/2008 | Andrews et al. | |
| 2008/0231849 A1 | 9/2008 | Myrick | |
| 2008/0276687 A1 | 11/2008 | Myrick et al. | |
| 2008/0309930 A1 | 12/2008 | Rensen | |
| 2009/0002697 A1 | 1/2009 | Freese et al. | |
| 2009/0015819 A1 | 1/2009 | Van Beek et al. | |
| 2009/0033933 A1 | 2/2009 | Myrick | |
| 2009/0073433 A1 | 3/2009 | Myrick et al. | |
| 2009/0097024 A1 | 4/2009 | Blackburn et al. | |
| 2009/0140144 A1 | 6/2009 | Myrick et al. | |
| 2009/0216504 A1 | 8/2009 | Priore et al. | |
| 2009/0219538 A1 | 9/2009 | Myrick et al. | |
| 2009/0250613 A1 | 10/2009 | Myrick et al. | |
| 2009/0299946 A1 | 12/2009 | Myrick et al. | |
| 2009/0316150 A1 | 12/2009 | Myrick et al. | |
| 2010/0042348 A1 | 2/2010 | Bakker | |
| 2010/0073666 A1 | 3/2010 | Perkins et al. | |
| 2010/0141952 A1 | 6/2010 | Myrick et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0211329 A1 | 8/2010 | Farquharson et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0328669 A1 | 12/2010 | Myrick et al. | |

FOREIGN PATENT DOCUMENTS

| | | |
|---|---|---|
| EP | 1974201 A1 | 10/2008 |
| EP | 2087328 A2 | 8/2009 |
| EP | 2140238 A1 | 1/2010 |
| JP | 57142546 A | 9/1982 |
| JP | 4001558 A | 1/1992 |
| JP | 07-053582 B2 | 6/1996 |
| JP | 11506206 | 6/1996 |
| JP | 9-3662 | 1/1997 |
| JP | 11506207 | 6/1999 |
| WO | 96/30746 | 10/1996 |
| WO | 2004/057284 A1 | 7/2004 |
| WO | 2005/062006 A1 | 7/2005 |
| WO | 2005/062986 A2 | 7/2005 |
| WO | 2006/031733 A2 | 3/2006 |
| WO | 2006/064446 A1 | 6/2006 |
| WO | 2006/137902 A2 | 12/2006 |
| WO | 2007/061435 A1 | 5/2007 |
| WO | 2007/061436 A1 | 5/2007 |
| WO | 2007/061437 A1 | 5/2007 |
| WO | 2007/062202 A1 | 5/2007 |
| WO | 2007/062224 A1 | 5/2007 |
| WO | 2007/064575 A1 | 6/2007 |
| WO | 2007/064578 A2 | 6/2007 |
| WO | 2008/002903 A2 | 1/2008 |
| WO | 2008/057912 A2 | 5/2008 |
| WO | 2008/057913 A2 | 5/2008 |
| WO | 2008/121684 A1 | 10/2008 |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysis by FTIR", Talanta, vol. 63, No. 4, pp. 1021-1025, 2004.

Inon et al., "Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy, Analytica Chimica Acta, vol. 544, No. 1-2, pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., *Infrared Detectors and Systems*, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of multivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-infrared point measurements", Proceedings of the SPIE, Bellingham, VA, US, vol. 4574, pp. 208-215, 2002.

(56) References Cited

OTHER PUBLICATIONS

O.S. Heavens, *Optical Properties of Thin Solid Films*, Dover Publications, Inc., Mineola, USA, pp. 62-81, 242-249, 1991.
S. Betancourt et al., "Analyzing Hydrocarbons in the Borehole", Oilfield Review, pp. 54-61, Autumn 2003.
D. Eastwood et al., "Field applications of stand-off sensing using visible/NIR multivariate optical computing", Ground and Air Pollution Monitoring and Remediation, SPIE vol. 4199, pp. 105-114, 2001.
Haibach et al., "On-line Reoptimization of Filter Designs for Multivariate Optical Elements", Applied Optics, vol. 42, No. 10, pp. 1833-1838, Apr. 1, 2003.
Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.
M.P. Nelson et al., "Multivariate optical computation for predictive spectroscopy", SPIE Vo. 3261, pp. 232-243, 1998.
O. Soyemi et al., "A Simple Optical Computing Device for Chemical Analysis", Proceedings of SPIE Vo. 4284, pp. 17-28, 2001.
O. Soyemi et al., "Design of angle tolerant multivariate optical elements for chemical imaging", Applied Optics, vol. 41, No. 10, pp. 1936-1941, Apr. 1, 2002.
O. Soyemi et al., "Nonlinear Optimization Algorithm for Multivariate Optical Element Design", Applied Spectroscopy, vol. 56, No. 4, pp. 477-487, 2002.
O. Soyemi et al., "Novel Filter Design Algorithm for Multivariate Optical Computing", Advanced Environmental and Chemical Sensing Technology, Proceedings of SPIE Vo. 4205, pp. 288-299, 2001.
Strausz et al., "About the Colloidal Nature of Asphaltenes and the MW of Covalent Monomeric Units", American Chemical Society, Energy and Fuels 16, No. 4, pp. 809-822, 2002 (abstract).
N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.
N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.
Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.
Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.
M.P. Nelson et al., "Multivariate optical computation for predictive spectroscopy", Analytical Chemistry, vol. 70, No. 1, pp. 73-82, Jan. 1, 1998.
M.P. Nelson et al., "Fabrication and evaluation of a dimension-reduction fiberoptic system for chemical imaging applications", Review of Scientific Instruments, vol. 70, No. 6, pp. 2836-2843, Jun. 1999.
M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.
M. Groner et al., "Identification of Major Water-Soluble Fluorescent Components of Some Petrochemicals", Marine Pollution Bulletin, vol. 42, No. 10, pp. 935-941, 2001.
M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.
M.L. Myrick et al., "Spectral tolerance determination for multivariate optical element design", Fresenius J Anal Chem, 369:351-355, 2001.
R.J. Priore et al., "Miniature Stereo Spectral Imaging System for Multivariate Optical Computing", Applied Spectroscopy, vol. 58, No. 7, pp. 870-873, 2004.
M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.
M.N. Simcock et al., "Precision in imaging multivariate optical computing", Applied Optics, vol. 46., No. 7, pp. 1066-1080, Mar. 1, 2007.
Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.
P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.
Mullins et al., "Gas-Oil Ratio of Live Crude Oils Determined by Near-Infrared Spectroscopy", Applied Spectroscopy, vol. 55, No. 2, pp. 197-201, 2001.
Dobrowolski, J.A., et al., "Refinement of Optical Multilayer Systems With Different Optimization Procedures," *Applied Optics*, vol. 29, No. 9, Jul. 1, 1990, pp. 2876-2893.
Sullivan, Brian T., et al., "Implementation of a Numerical Needle Method for Thin-Film Design," *Applied Optics*, vol. 35, No. 28, Oct. 1996, pp. 5484-5492.
The Chemistry of Ferric Chloride; Printmaking Today, vol. 4, No. 2, 1995; Cello Press Ltd., Oxon, UK, 2 pages.
MSDS Hyper Glossary is a website http://www.ilpi.com/msds/ref/index.html , Safety Emporium Laboratory and Safety Supplies, retrieved on Feb. 10, 2012, 4 pages.
Handbook of Polymer Coating for Electronic Chemistry and Applications, 2nd ed., 1990.
Ryabenko, A.G., et al., "An Algorithm for Constructing the Basis of Optimal Linear Combinations . . . ", Pattern Recognition and Image Analysis, vol. 3, No. 1, 1993, 12 pages.
Moravskii, A.P., "Spectrophotometrtc Determination of the Yield of the C60 and C70 Fullerenes in Electric Arc Synthesis under Helium", Journal of Analytical Chemistry, vol. 53, No. 12, 1998, 8 pages.
MSDS No. F1080, Material Safety Data Sheet, Mallinckrodt Baker, Inc., Feb. 18, 2003, 6 pages.
Vasil'Ev, G.K., et al., "Rotational and Vibrational Deactivation of Excited HF Molecules", Soy. Physics—JETP, vol. 41, No. 4, 1976, pp. 617-621.
Ryabenko, A.G., et al., "Numerical Study of a Pattern Recognition Multispectral System With Optimal Spectral Splitting," Pattern Recognition and Image Analysis, vol. 1, No. 3, 1991, 10 pages.
PCT International Search Report/Written Opinion mailed Apr. 16, 2008, in related Application No. PCT/US2007/083291.

\* cited by examiner

MULTI-ANALYTE OPTICAL COMPUTING SYSTEM

This application claims priority under 35 USC 119(e) of Provisional Patent Application Ser. No. 60/856,191 filed Nov. 2, 2006, entitled "MULTI-ANALYTE OPTICAL COMPUTING SYSTEM," which is hereby incorporated by reference in its entirety.

FIELD OF THE INVENTION

The present subject matter relates to system design, fabrication and operation of multivariate optical elements. More particularly, the present subject matter relates to methodologies of using multivariate optical computing systems to illuminate a sample such that information about the sample can be analyzed from reflected or transmitted light in real time or near real time.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, measurement of light intensity may be difficult to convert to information due to contained interfering data. That is, several factors may contribute to the intensity of light, even in a relatively restricted wavelength range. It is often impossible to adequately measure the data relating to one of these factors since the contributions from other factors may be unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information regarding the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{("Equation 1")}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood by those of ordinary skill in this art. Briefly, however, principal component analysis is a dimension reduction technique, which takes in spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(``Equation 2'')}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multiwavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or co-adds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various implementations of Optical Analysis Systems have been developed to enhance measurement accuracy, no design has emerged that generally encompasses all of the desired characteristics as hereafter presented in accordance with the subject technology.

SUMMARY OF THE INVENTION

In view of the recognized features encountered in the prior art and addressed by the present subject matter, an improved methodology for high-speed processing and monitoring of a plurality of sample portions of products has been developed. In accordance with an exemplary configuration of the present subject matter, products may be moved past an inspection point while illuminating at least one portion of the sample product with a spectral-specific light through an optic window. The optical window may be configured to focus the spectral-specific light onto a sample portion at the inspection point. In an exemplary embodiment, the sample products may include pharmaceutical products.

In one representative configuration, light reflecting from the sample, which contains information about the sample, passes through a chopper wheel and onto a detector. As the chopper wheel rotates, the light passes through different elements depending on the orientation of the wheel at a given time. Hence the signal at the detector changes sequentially as light passes through the different multivariate optical elements or reference elements or the light is blocked (where the spokes on the chopper wheel block the light). A different signal is produced for each element. These signals are used to determine at high speed one or more selected properties of the portion as it moves past the inspection point based upon the detector output.

In an exemplary arrangement, the sample portions may comprise pharmaceutical tablets, trays or other containers of powders, or partially- or fully-enclosed sample containers at least partially transparent to light focused onto the sample portion. In an exemplary configuration, sample portions may be moved past the inspection point at a rate between about one portion/second and about five portions/second, with monitoring occurring in real-time at high speed.

In accordance with aspects of certain other embodiments of the present subject matter, a method of high-speed processing and monitoring includes moving a product past an inspection point and illuminating at least a portion of the product with a light. Light reflecting from the sample, which contains information about the sample, passes through a chopper wheel and onto a detector. As the chopper wheel rotates, the light passes through different elements depending on the orientation of the wheel at a given time. Hence the signal at the detector changes sequentially as light passes through the different multivariate optical elements or reference elements or the light is blocked where the spokes on the chopper wheel block the light. A different signal is produced for each element. These signals are used to determine, at high speed, one or more selected properties of the sample portion as it moves past the inspection point based upon the detector output. The product in this aspect may be, for example, a pharmaceutical tablet or powder, a food material, a chemical, a liquid, a gas, an emulsion, a solution, and/or a mixture.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters throughout the present specification and appended drawings is intended to represent same or analogous features or elements of the invention.

DETAILED DESCRIPTION OF THE INVENTION

As discussed in the Summary of the Invention section, the present subject matter is particularly concerned with an improved methodology for high-speed processing and monitoring of a plurality of sample product portions.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

As used herein, the term "light" is broadly used to mean any form of radiation or radiative energy including, but not limited to, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample.

As used herein, the sample being evaluated can be a solid or a fluid including, but not limited to, a powder, a pharmaceutical powder mixed with lactose and other excipient materials, a chemical, a polymer, a petroleum product, a solution, a dispersion, an emulsion and combinations of these solids and fluids.

Figure 1:
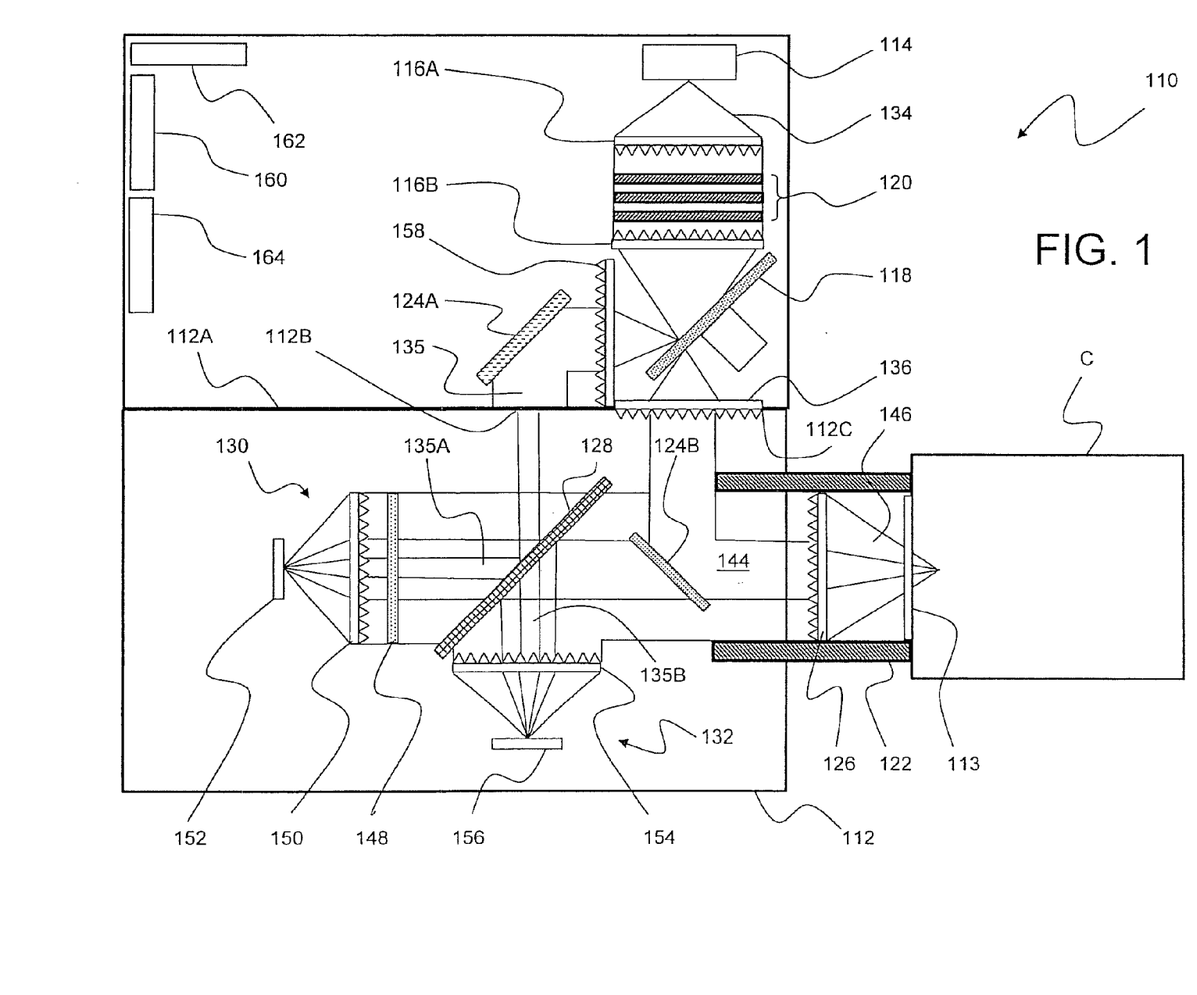
FIG. 1 is schematic plan view of a real time measurement system according to the general concept of the present technology.

Reference will now be made in detail to the presently preferred embodiments of the subject optical computing system. Referring now to the drawings, FIG. 1 illustrates an optical analysis system 110 generally depicting the concept of the present subject matter. As shown in FIG. 1, optical analysis system 110 broadly includes a housing 112, an illumination or light source 114, a chopper wheel 118, one or more spectral elements 120, a focusing lens 126, a beam splitter 128, a first detector 130 including a multivariate optical element 148, and a second detector 132. Optical analysis system 110 further includes representatively illustrated electrical connection 160, pressurization sensor 162 and purge gas assembly 164. These representatively illustrated components are well understood by those of ordinary skill in the present art and, therefore, further description is not deemed necessary to understand and practice these aspects of the present subject matter.

With more particular reference to FIG. 1, illumination source 114 provides a light 134, which passes through a collecting Fresnel lens 116A and into and through spectral element(s) 120. In an exemplary configuration, illumination source 114 may be rated for at least about 10,000 hours of operation, which alleviates a need for redundant illumination sources though such redundant sources may be provided if desired. Further, in the illustrated exemplary configuration, the collecting Fresnel lens 116A is sized to be about 1.5 square inches and is spaced about 0.6 inches from the illumination source 114. Those of ordinary skill in the art will appreciate that these dimensions can be adjusted according to particular system requirements and are thus not meant as limitations of the present subject matter.

As further shown in FIG. 1, light 134 passes through spectral elements 120, which filter out undesired wavelengths to define a desired spectral region in order to target a particular chemical material of interest. In an exemplary configuration the spectral region may correspond to, 1500-2000 nm. Light 134 is focused by focusing Fresnel lens 116B, which, in an exemplary configuration may also be sized to be about 1.5 square inches and spaced about 1 inch from the chopper wheel 118. As shown, the chopper wheel 118 reflects a portion of light 134 as a calibration or reference light 135 and passes another portion as transmitted light 144.

Calibration light 135 is collimated by lens 158 before reflecting from a first mirror 124A through an adjustable aperture 112B in a bulkhead 112A of the housing 112. Aperture 112B is adjustable to control the amount of the calibration light 135 passing through the aperture. Finally, calibration light 135 impinges on beam splitter 128 thereby sending a portion 135A of calibration light 135 to the first MOE detector 130 and a portion 135B of calibration light 135 to the second or baseline detector 132.

With further reference to FIG. 1, it may be seen that transmitted light 144 passes from the chopper wheel 118 into a collimating Fresnel lens 136, which in this exemplary configuration is sized to be about 1.5 square inches and is spaced about 0.6 inches from the chopper wheel 118. Transmitted light 144 passes through another adjustable aperture 112C in the bulkhead 112A and impinges upon a second mirror 124B, which directs transmitted light 144 toward a sample in a container C. In an exemplary configuration, container C may correspond to a mixing vat or blender. Those of ordinary skill in the art will appreciate that "container" C could correspond to a conveyor belt or other device for holding or transporting the sample and is thus not limited to an enclosed container.

As further illustrated in FIG. 1, transmitted light 144 is focused by focusing Fresnel lens 126, which in this exemplary configuration may be round and about 15/16 inches in diameter and is adjustable with an inner tube 122. Also in this exemplary configuration, lens 126 may be positioned about 0.6 inches from an outer surface of the container C. As shown, transmitted light 144, now focused by Fresnel lens 126, passes through a transmissive window 113. In an exemplary configuration transmissive window 113 may be approximately 1 inch in diameter and include an anti-reflective (AR) coating disposed on one or both sides of the window 113. The AR coating ensures that the chemical process in the container C does not interfere with the measuring process of optical analysis system 110. Thus, transmitted light 144 enters the container C and reflects from the sample as carrier light 146. The sample can be a moving mixture such as aspirin and an excipient being blended in real time, or a plurality of tablets passing by on a conveyor belt at high speed.

Referring further to FIG. 1, it will be seen that carrier light 146 is directed by the tube 122 in a direction of the first detector 130. Eventually, carrier light 146 impinges on beam splitter 128 so that a portion of carrier light 146 passes in a direction of detector 132 for baselining with portion 135B of calibration light 135. Another portion of carrier light 146 passes through MOE 148, which as noted above, has been selected for the chemical of interest based on the various components of the system 110. Finally, that portion of carrier light 146, having passed through the MOE 148, is focused by lens 150 and received by the detector 152. As described above, the two signals collected by the detectors 152 and 156 can be manipulated, e.g., mathematically, to extract and ascertain information about the sample carried by the carrier light 146.

In accordance with the present subject matter, further exemplary embodiments of optical computing systems based on the optical computational method previously described with reference to FIG. 1 are described herein after with reference to FIGS. 2-6. In general, these further embodiments differ from that described in FIG. 1 in that they employ a single detector with a moving holder, such as a chopper wheel, containing several multivariate optical elements and reference materials. In accordance with these embodiments of the present subject matter, the chopper wheel rotates so that the various elements pass in front of the detector in sequence enabling the use of several optical elements in the same unit. The chopper wheel containing the multivariate optical elements (MOEs) and spectral elements must rotate fast enough to compensate for sample movement and various light fluctuations. Each multivariate optical element and associated reference element is designed for measurement of a specific property. Because the spectral elements and multivariate optical elements are used as a combination for a given analyte, several configurations are presented each illustrating variations in spectral element installation.

Figure 2:
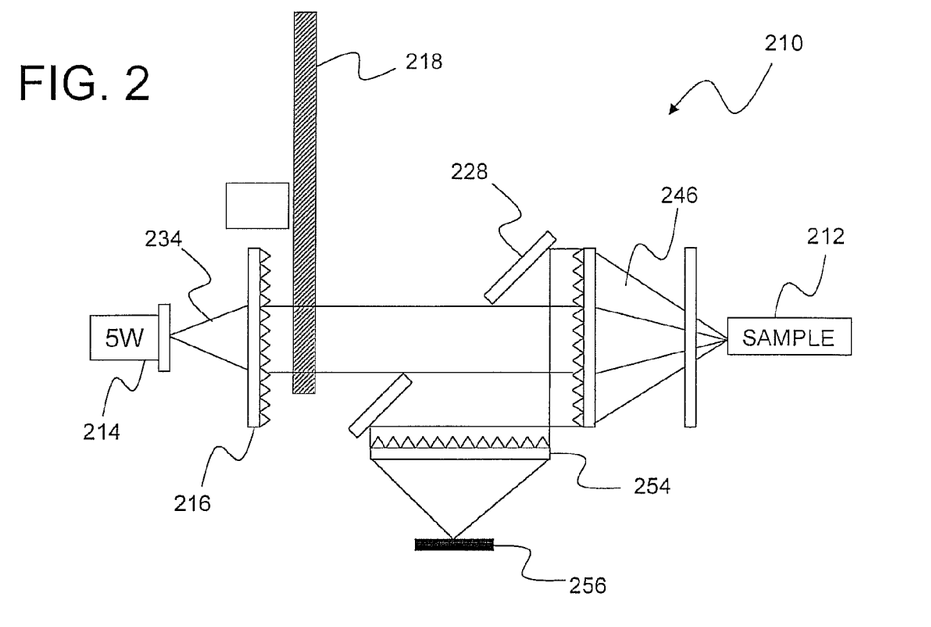
FIG. 2 is a schematic view of a real time measurement system according to the present subject matter illustrating a focusing lens at the illumination source.

Each of FIGS. 2-6 illustrate further embodiments of optical computing systems operating in accordance with the general concept of the optical computing system illustrated in FIG. 1. With reference to FIG. 2 a first exemplary embodiment of an optical computing system 210 constructed in accordance with the present subject matter and employing a single detector 256 will be described. As illustrated in FIG. 2, lens 216 is configured to collect light 234 emitted by illumination source 214 and to direct it towards sample 212 by way of chopper wheel 218 and mirror 228. Reflected light 246 from sample 212 reflects from mirror 228 toward detector 256 by way of focusing lens 254. In an exemplary configuration, mirror 228 may be oval, however, other shapes, e.g., round, may also be employed. Further different mirror configuration may include one where illuminating light passes through an outer annual region to illuminate the sample as opposed to the central portion illustrated, while the turning mirror returns the inner portion of the light toward the detector.

Figure 3:
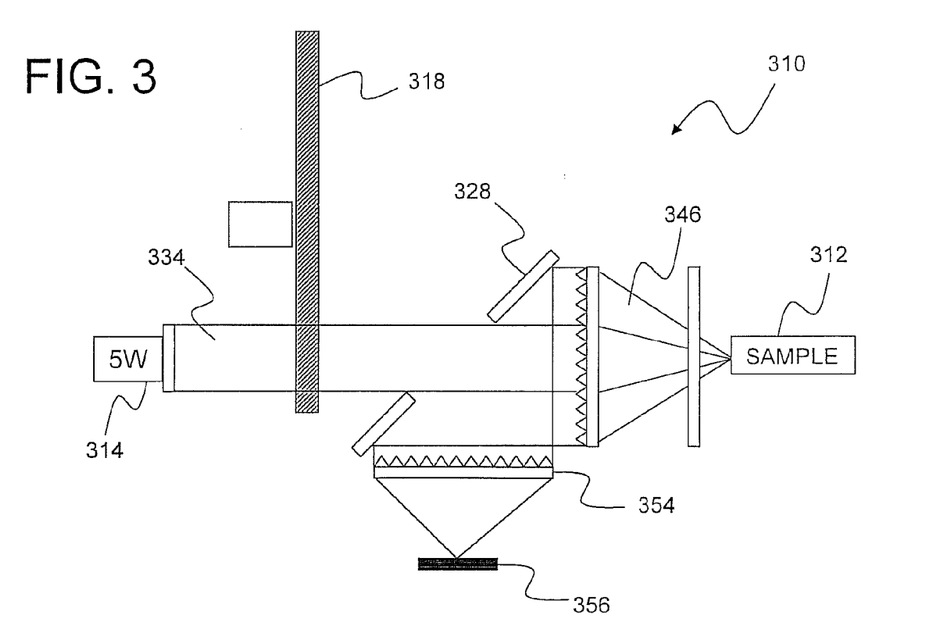
FIG. 3 is a schematic view of a real time measurement system according to the present subject matter illustrating collimated light at the illumination source.

FIG. 3 illustrates a configuration identical to that of FIG. 2 except that illumination source 314 produces collimated light. Remaining reference numerals in FIG. 3 correspond directly to those of FIG. 2 except for being designated in the 300's series as opposed to the 200's series of FIG. 2 and will thus not be further described. It should be appreciated that as illumination source 314 produces collimated light, and equivalent of FIG. 2,'s lens 216 is not required.

Figure 4:
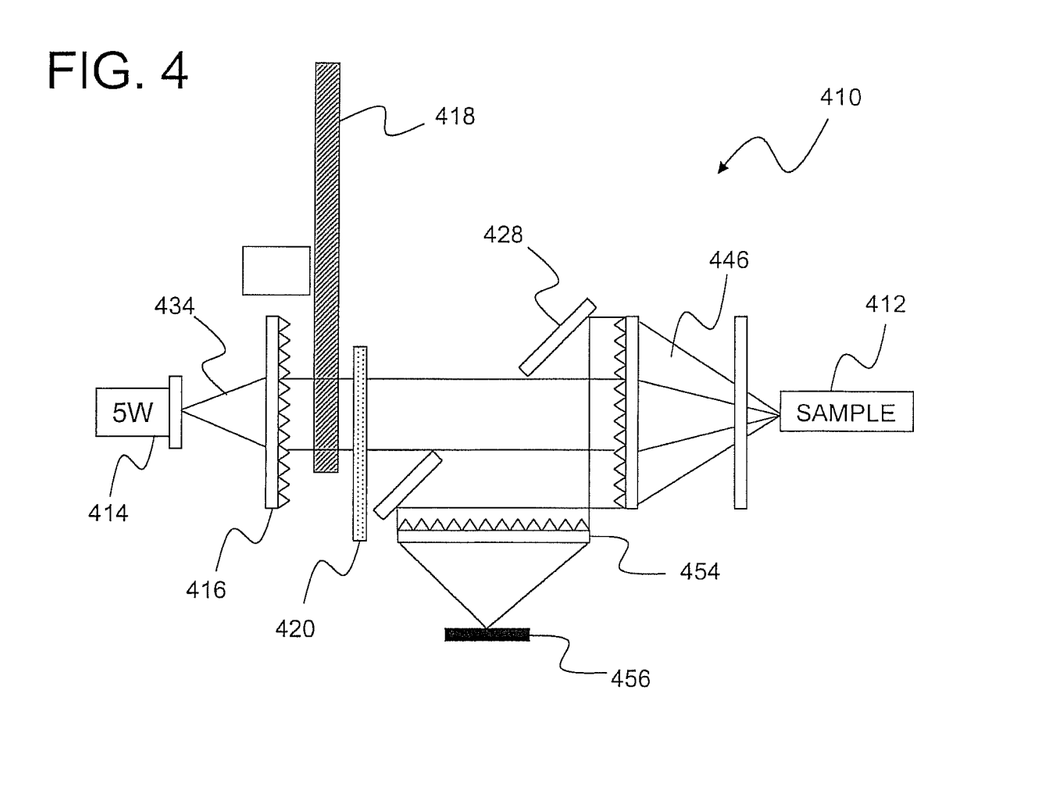
FIG. 4 is a schematic view of a real time measurement system according to the present subject matter illustrating a set of common spectral elements for all the measurements.
Figure 6:
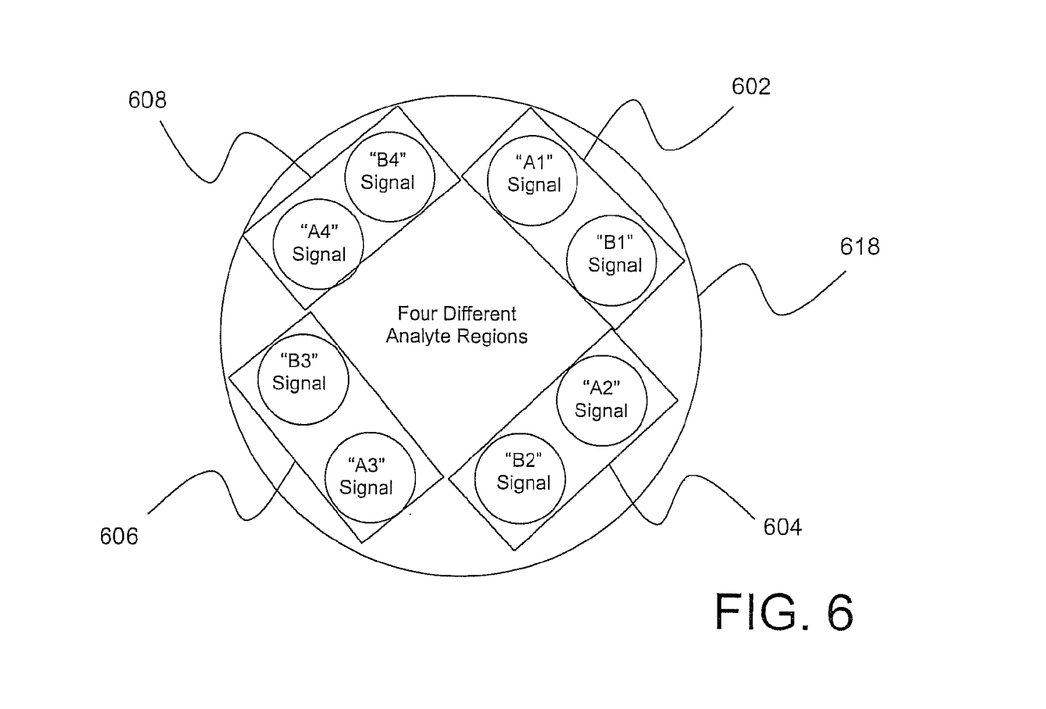
FIG. 6 is a schematic view of a chopper wheel illustrating the inclusion of separate spectral elements for each of four analytes being measured.

The configurations illustrated in FIGS. 2 and 3 employ spectral elements located on their respective chopper wheels 218, 318 as illustrated by rectangles 602, 604, 606, 608 on chopper wheel 618 of FIG. 6. As illustrated in FIG. 6, spectral elements within rectangle 602 are employed for a first analyte, while spectral elements within rectangles 604, 606, and 608 are employed for second, third, and forth analytes, respectively. If the same spectral elements are used for all analytes, then a common spectral element 420 can be employed as shown in FIG. 4. It should be appreciated by those of ordinary skill in the art that the components illustrated in FIG. 4 are generally identical to those of FIGS. 2 and 3 and are thus identified with equivalent but 400's series numbers. Those of ordinary skill in the art will also appreciate that the embodiment illustrated in FIG. 4 may also be modified in a manner like that of the embodiment of FIG. 3 to provide collimated light in place of the illustrated light source 414 and collimating lens 416.

Figure 5:
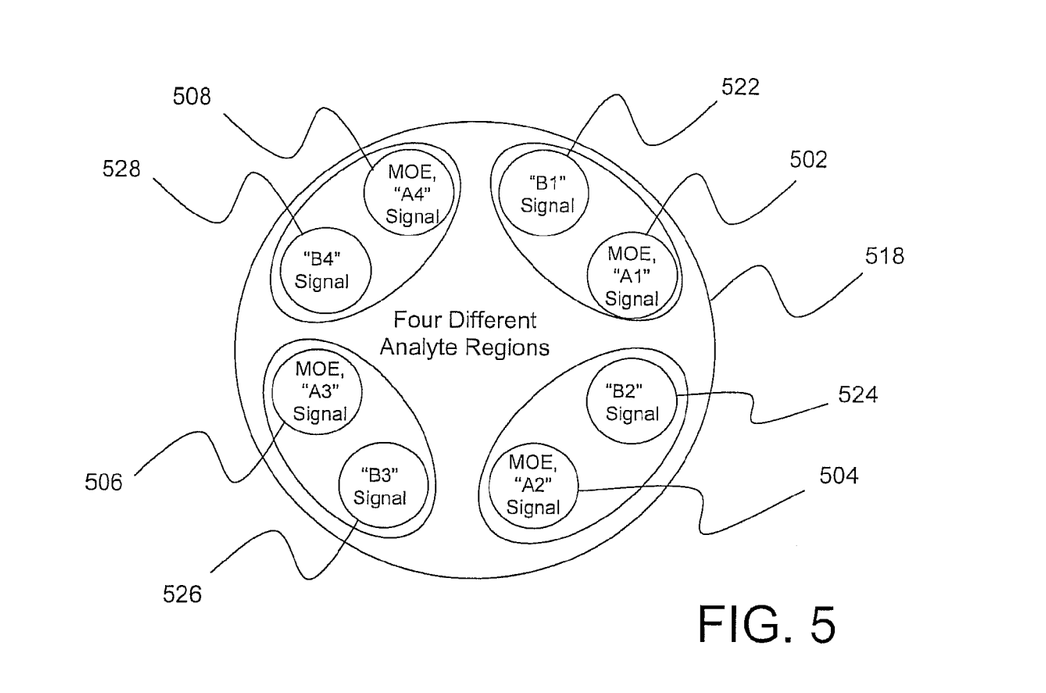
FIG. 5 is a schematic view of the chopper wheel containing several multivariate optical elements (A) and reference elements (B)

FIG. 5 illustrates an exemplary configuration of a chopper wheel 518 containing multivariate elements 502, 504, 506, 508 and reference elements 522, 524, 526, 528 for each of four independent analytes. FIG. 6 illustrates an opposite side view of the same chopper wheel shown in FIG. 5 with the spectral elements indicated as rectangles. In this example, there are separate spectral element units for each of four analytes.

In accordance with the single detector system of the present subject matter, "A" and "B" signals for each multivariate optical element are collected in sequence. As illustrated in FIG. 5, the signal sequence produced by chopper wheel 518 (FIG. 5) would correspond to Analyte 1-B signal, Analyte 1-A signal, Analyte 2-B signal, Analyte 2-A signal, Analyte 3-B signal, Analyte 3-A signal, Analyte 4-B signal, Analyte 4-A signal, Analyte 1-B signal, and so forth. Multivariate optical element signal and reference signal calculations conducted on these signals are performed in the time domain. This is important to make sure that the Analyte 1 multivariate optical element (A) signal is compared to the Analyte 1 reference (B) signal.

The functionality of MOC system 110 (FIG. 1) and the single detector embodiments as described above allow for the collection of the entire spectral range of testing simultaneously. This fact is notably different than either a system based on either a scanning lamp or detector system or a discrete diode array detection system. The ability to monitor over the complete spectral range of interest opens up a redefinition of the term "real-time" measurement and analysis. For instance, true real-time process measurements are possible.

In accordance with present disclosure, "real time" refers to obtaining data without delays attendant to collecting samples or delays due to lengthy computer processing of measurement signals. In accordance with the subject matter described herein, process data can be obtained in an instantaneous or near-instantaneous manner through using the disclosed measurement techniques to directly monitor materials of interest while such materials are undergoing process steps. Long delays due to processing of measurement signals are avoided by optically processing the light as it is reflected from the material(s) of interest.

Although specific examples disclosed herein describe monitoring blending of a powdered material and examining solid tablets, the general concept can be extended to other phases. The present system can be utilized in analyzing solids, solutions, emulsions, gases, and dispersions, for example. In addition, while exemplary embodiments discussed herein use reflectance measurements, measurements in a transmission or transflectance mode would also be appropriate and is fully contemplated by the present disclosure.

One of ordinary skill in the art will recognize that differing applications may require modifications and alterations to certain components in order to take full advantage of the presently-disclosed systems, all of which adjustments would be well within the capability of those of ordinary skill in the art given an understanding of the present disclosure. For instance, more diffusion of light has been observed in solid powders relative to liquids; accordingly, different lenses may be needed when a liquid is monitored in order to account for such variations and achieve more accurate measurements.

The presently-disclosed technology can be applied to real-time measurements for a range of industrial applications. These include, but are not limited to, monitoring of the blending of pharmaceutical powders, including excipients, additives, and active pharmaceutical materials; blending of other powders, including food and chemicals; monitoring dispersions and bi-phasic mixtures (such as insulin, emulsions); and oil and gas applications, including analyzing water content in oil, or oil content in water.

Inclusion of a transmissive window provides physical separation between the measuring device and the process or material being tested. Therefore, this window allows for in-line measurement and/or non-invasive measurement of parameters such as chemical functionality, including alcohol content of petroleum fractions or tackifier resins. Environmental applications are also conceivable, such as stack gas analysis, including measurement of NOx, SOx, CO, CO2, or other gases in a gas stream; wastewater analysis and treatment monitoring; and hazardous substance monitoring applications such as mercury vapor detection.

As noted above, MOC technology in accordance with present disclosure can be used to monitor a wide variety of materials as the materials are subjected to different processes. For instance, the mixing of powders can be monitored. As materials are blended, the existing art does not allow for continuous, real-time, in-line measurement. Current limitations are the result of several factors including: moving of the powders being measured during the course of data acquisition and the need to connect analytical equipment to the measurement point using fiber optic cables. This optical analysis system is designed to allow for instantaneous measurement using a measurement point located on the vessel.

Other embodiments of the present subject matter provide for real time measurement of flowing materials. In such embodiments, sampling window(s) may be located on a pipe or vessel such that interrogating illumination can be applied to the material. For instance, a port could be included on a pipe to allow for sampling of the material inside the pipe. The window may be positioned directly on the pipe, or on a small diversion away from the main flow path, as appropriate under the circumstances. Such embodiments could also include sampling of vapor systems within a stack to monitor combustion gases or flowing process stream such as water containing other materials.

Still further embodiments of the present subject matter provide real time measurement of materials in containers, such as vials or bins where the container is either at least partially open to the outside environment or transmissive to the sampling illumination. Such containers could be stationary or in motion. A container could also include a conveyor or trough carrying material. Typical applications could include the monitoring the progress of a chemical reaction or the content of samples moving past a measurement location.

The present subject matter may be better understood from the following tests and examples. In a first example, a breadboard system was constructed and used to test a mixture of powders. The first system components included a 20W Gilway lamp and employed a 5 mm deuterium oxide ($D_2O$) and 5 mm Germanium spectral elements. A fiber optic probe was employed as an optical window while an InAr detector was used for measurements. For this example, a powdered sample with a known composition was placed in a dish and the fiber optic probe was placed in contact with the powder. The output of the detectors was monitored and recorded.

In a second example, a system was constructed and used to make static measurements on aspirin/lactose. The second example system employed components identical to those of the first sample except for the detector where a PbS detector from New England Photoconductor was employed instead of the InAr detector. For this example, a powdered sample with a known composition was placed in a dish and the system light beam was focused on the powder. The output of the detectors was monitored and recorded. Aspirin/lactose samples covering the range of 100% aspirin to 100% lactose were tested.

In a third example, a system similar to that employed in the second example was employed except that a sapphire window was employed to gain access to the test material light borne data. In this example, Aspirin/Lactose testing was performed using a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

Although the present subject matter has been described in such a way as to provide an enabling disclosure for one skilled in the art to make and use the invention, it should be understood that the descriptive examples are not intended as limitations of the subject matter as described herein and shown in the Figures. For instance, the housing can be shaped as a square, an oval, or in a variety of other shapes. Further, a variety of light sources can be substituted for those described above. It is intended to claim all such changes and modifications as fall within the scope of the appended claims and their equivalents. Thus, while exemplary embodiments of the invention have been shown and described, those skilled in the art will recognize that changes and modifications may be made to the foregoing examples without departing from the scope and spirit of the present subject matter.

What is claimed is:

1. A method for high-speed analysis of product samples comprising:
   transmitting an illumination light through a analyte multivariate optical element to form an analyte light, the multivariate optical element being positioned on a chopper wheel;
   illuminating a sample at an inspection point with the analyte light;
   transmitting the illumination light through a reference optical element to form a reference light different from the analyte light, the reference optical element being positioned on the chopper wheel and configured to correspond to the multivariate optical element;
   illuminating the sample with the reference light;
   providing a light sensitive detector, the detector producing an output signal based on received light;
   directing light from the sample toward the light sensitive detector, the light from the sample carrying information about the sample; and
   analyzing output signals produced by the detector, the analysis being based on a comparison of an output signal produced by the analyte light and an output signal produced by the reference light.

2. The method of claim 1, wherein the sample is at least one of a pharmaceutical tablet, a pharmaceutical powder, a food material, a chemical, a liquid, a gas, an emulsion, a solution, or a mixture thereof.

3. The method of claim 1, wherein the sample is a powder mixture in a closed container, the container being at least partially transparent to the illumination light.

4. The method of claim 1, further comprising:
   moving the sample past the inspection point.

5. The method of claim 1, wherein directing light from the sample comprises directing light reflected from the sample.

6. The method of claim 1, wherein directing light from the sample comprises directing light transmitted through the sample.

7. The method of claim 1, wherein illuminating the sample with the analyte light comprises illuminating the sample with a spectral-specific light.

8. The method of claim 7, further comprising:
   illuminating the sample through an optic window, the optic window being configured to focus the spectral-specific light onto a sample portion at the inspection point.

9. The method of claim 1, wherein the sample comprises a plurality of discrete portions.

10. The method of claim 9, wherein the plurality of discrete portions are disposed in closed containers, the containers at least partially transparent to the spectral-specific light.

11. The method of claim 1, wherein:
    transmitting the illumination light through the analyte multivariate optical element comprises directing the illumination light through a plurality of multivariate optical elements; and
    transmitting the illumination light through the reference optical element comprises directing the illumination light through a plurality of reference optical elements.

12. The method of claim 11, wherein the illumination light is transmitted alternately through differing multivariate optical elements and corresponding reference optical elements in sequence.

13. The method of claim 1 further comprising determining a specific property of an analyte in the sample associated with the multivariate optical element and the reference optical element.

14. The method of claim 13 wherein the analyte includes a gasoline.

15. The method of claim 14 wherein the specific property of the analyte is an octane rating of the gasoline.

16. A system for high-speed analysis of samples comprising:
    an illumination source to provide an illumination light to at least a sample at an inspection point, the sample comprising at least one analyte;
    a light sensitive detector to produce an output based on a received light;
    a chopper wheel comprising:
       a multivariate optical element placed between the illumination source and the sample; and
       a reference optical element placed between the illumination source and the sample, wherein the reference optical element corresponds to the multivariate optical element; and
    an optical element to direct light from the sample to the light sensitive detector;
    wherein the multivariate optical element and the reference optical element are selected for measurement of a specific property of the analyte, and for illuminating the sample with an analyte light different from a reference light.

17. The system of claim 16 further comprising a plurality of multivariate optical elements, each of the plurality of optical elements associated with a reference optical element, the multivariate optical element and the reference optical element selected to measure a specific property of the analyte.

18. The system of claim 16 wherein the analyte comprises at least a gasoline sample.

19. The system of claim 18 wherein the specific property is an octane rating of the gasoline sample.

* * * * *